(12) United States Patent
D'Angelo

(10) Patent No.: US 8,955,368 B2
(45) Date of Patent: Feb. 17, 2015

(54) APPARATUS AND METHOD FOR AEROSOL COLLECTION AND FLUID ANALYSIS

(75) Inventor: John P. D'Angelo, Medford, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 272 days.

(21) Appl. No.: 13/238,399

(22) Filed: Sep. 21, 2011

(65) Prior Publication Data

US 2013/0067993 A1    Mar. 21, 2013

(51) Int. Cl.
*G01N 1/00* (2006.01)
*G01N 1/22* (2006.01)

(52) U.S. Cl.
CPC .................. *G01N 1/2208* (2013.01)
USPC ....... 73/28.04; 73/863.21; 73/1.02; 73/25.05; 73/29.05; 73/30.04; 222/236; 222/237; 222/271; 222/296

(58) Field of Classification Search
CPC .......... G01N 15/0656; G01N 15/0205; G01N 15/12; G01N 2015/1062; G01N 15/1056; G01N 29/032; G01N 2015/1087; F01N 2560/05; B01L 2400/0487; G06Q 10/1057; A01N 43/56; B60W 10/06; B60W 10/08; C07D 231/21
USPC ............ 73/863.21, 1.02, 25.05, 29.05, 30.04, 73/31.05, 235; 222/1, 236, 237, 271, 296
See application file for complete search history.

(56) References Cited

U.S. PATENT DOCUMENTS

| | | | |
|---|---|---|---|
| 3,838,972 A * | 10/1974 | Richards et al. .............. 436/100 |
| 4,461,183 A * | 7/1984 | Wedding .................... 73/863.21 |
| 4,570,494 A * | 2/1986 | Dunn et al. ................. 73/863.22 |
| 4,923,491 A * | 5/1990 | Lawless et al. .................. 55/409 |
| 5,288,256 A | 2/1994 | Lee et al. |
| 5,332,550 A * | 7/1994 | Booker ........................... 422/83 |
| 5,768,918 A | 6/1998 | Mckibben |
| 6,042,885 A | 3/2000 | Woollard et al. |
| 6,087,114 A | 7/2000 | Rider |
| 6,248,542 B1 | 6/2001 | Rider et al. |
| 6,321,608 B1 * | 11/2001 | Wagner et al. ............ 73/863.21 |
| 7,172,096 B2 | 2/2007 | O'Dougherty |
| 7,214,346 B2 | 5/2007 | Harper et al. |
| 7,214,348 B2 | 5/2007 | Desmond et al. |
| 7,418,977 B2 | 9/2008 | Ducreëet al. |
| 7,422,860 B2 | 9/2008 | Schwoebel et al. |

(Continued)

OTHER PUBLICATIONS

Colwell, Gene T., et al., "Laminar viscous flow fields in moving curved channels", Computers & Fluids, vol. 5, Issue 2 (Jun. 1977), pp. 99-112.

*Primary Examiner* — Peter Macchiarolo
*Assistant Examiner* — Mohammed Keramet-Amircola
(74) *Attorney, Agent, or Firm* — Modern Times Legal; Robert J. Sayre

(57) ABSTRACT

An apparatus for aerosol collection and fluid analysis includes a rotary motor, an aerosol-collection disk configured for mounting on the rotary motor, and a fluid-analysis disk that is also configured for mounting on the rotary motor. The aerosol-collection disk includes at least one interior inlet, at least one peripheral outlet and a passage coupling the interior inlet with the peripheral outlet, and a particle collector opposite the peripheral outlet. The fluid-analysis disk includes at least one fluid in each of a first reservoir and in a second reservoir on or in the fluid-analysis disk and offset from a central axis of the disk, wherein each reservoir has an outlet and a stopper in the outlet of each reservoir to seal the reservoirs; and release of the fluids from the reservoirs is spin-induced.

14 Claims, 13 Drawing Sheets

(56) References Cited

U.S. PATENT DOCUMENTS

| | | | |
|---|---|---|---|
| 7,472,612 B2* | 1/2009 | Zaromb et al. | 73/863.21 |
| 8,475,577 B2* | 7/2013 | Novosselov et al. | 96/413 |
| 2008/0269077 A1 | 10/2008 | Lee et al. | |
| 2012/0024083 A1* | 2/2012 | Wo et al. | 73/863.21 |

* cited by examiner

APPARATUS AND METHOD FOR AEROSOL COLLECTION AND FLUID ANALYSIS

GOVERNMENT SUPPORT

This invention was made with government support under Contract No. FA8721-05-C-0002 awarded by the U.S. Air Force. The government has certain rights in this invention.

BACKGROUND

A variety of contexts exists wherein air sampling and analysis of particulates or organisms suspended therein is desirable. Exemplary applications where air sampling and analysis can serve to protect human health include detection of pathogens in air supplies and air-quality monitoring in, e.g., office buildings, public venues, factories, mines and ships.

SUMMARY

Apparatus and methods for aerosol collection and fluid analysis are described herein. Various embodiments of the apparatus and methods may include some or all of the elements, features and steps described below.

An apparatus for aerosol collection and fluid analysis includes a rotary motor, an aerosol-collection disk configured for mounting on a rotary stage of the motor, and a fluid-analysis disk that is also configured for mounting on the rotary motor. The aerosol-collection disk includes at least one interior inlet, at least one peripheral outlet and at least one passage coupling the interior inlet with the peripheral outlet, and a particle collector opposite the peripheral outlet. The fluid-analysis disk includes at least one fluid in each of a first reservoir and a second reservoir on or in the fluid-analysis disk and offset from a central axis of the disk, wherein each reservoir has an outlet and a stopper in the outlet of each reservoir to seal the reservoirs; and release of the fluids from the reservoirs via centrifugal force is spin-induced by the rotary motor.

The fluid-analysis disk can be of any of the following designs. In a first embodiment, the outlet of the first reservoir faces a first direction relative to the central axis; and the outlet of the second reservoir faces a second direction (distinct from the first direction) relative to the central axis. In a second embodiment, the first reservoir is offset from the central axis of the disk by a first radius; and the second reservoir is offset from the central axis of the disk by a second shorter radius. In a third embodiment, the first stopper in the first reservoir has a first release or sealing force; and the second stopper in the second reservoir has a second release or sealing force, wherein the first release or sealing force is less than the second release or sealing force.

Embodiments of the apparatus and methods can provide air-quality monitoring with the following advantages over conventional air-quality monitoring systems that use vacuum or blower systems for aerosol collection: simple design and operation; high efficiency; reduced cooling; low weight and volume; high portability; low expense for the apparatus and its operation.

Figure 1:
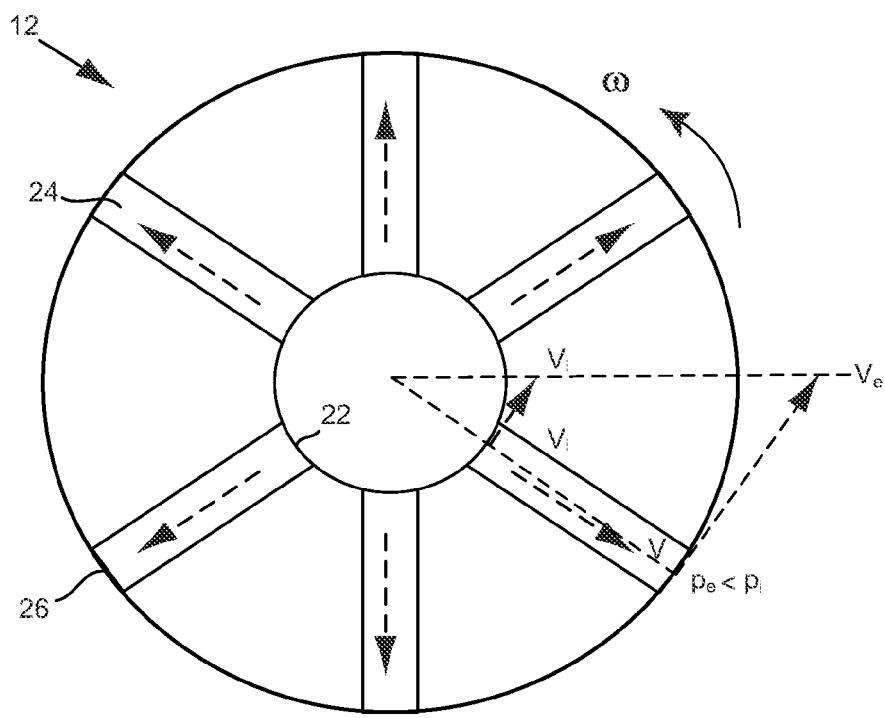
FIG. 1 depicts radial flow through a spinning aerosol-collection disk.

In the accompanying drawings, like reference characters refer to the same or similar parts throughout the different views; and apostrophes are used to differentiate multiple instances of the same or similar items sharing the same reference numeral. The drawings are not necessarily to scale, emphasis instead being placed upon illustrating particular principles, discussed below.

DETAILED DESCRIPTION

The foregoing and other features and advantages of various aspects of the invention(s) will be apparent from the following, more-particular description of various concepts and specific embodiments within the broader bounds of the invention(s). Various aspects of the subject matter introduced above and discussed in greater detail below may be implemented in any of numerous ways, as the subject matter is not limited to any particular manner of implementation. Examples of specific implementations and applications are provided primarily for illustrative purposes.

Unless otherwise defined, used or characterized herein, terms that are used herein (including technical and scientific terms) are to be interpreted as having a meaning that is consistent with their accepted meaning in the context of the relevant art and are not to be interpreted in an idealized or overly formal sense unless expressly so defined herein. For example, if a particular shape is referenced, the shape is intended to include imperfect variations from ideal shapes, e.g., due to machining tolerances.

Although the terms, first, second, third, etc., may be used herein to describe various elements, these elements are not to be limited by these terms. These terms are simply used to distinguish one element from another. Thus, a first element, discussed below, could be termed a second element without departing from the teachings of the exemplary embodiments.

Spatially relative terms, such as "above," "below," "left," "right," "in front," "behind," and the like, may be used herein for ease of description to describe the relationship of one element to another element, as illustrated in the figures. It will be understood that the spatially relative terms, as well as the illustrated configurations, are intended to encompass different orientations of the apparatus in use or operation in addition to the orientations described herein and depicted in the figures. For example, if the apparatus in the figures is turned over, elements described as "below" or "beneath" other elements or features would then be oriented "above" the other elements or features. Thus, the exemplary term, "above," may encompass both an orientation of above and below. The apparatus may be otherwise oriented (e.g., rotated 90 degrees or at other orientations) and the spatially relative descriptors used herein interpreted accordingly.

Further still, in this disclosure, when an element is referred to as being "on," "connected to" or "coupled to" another element, it may be directly on, connected or coupled to the other element or intervening elements may be present unless otherwise specified.

The terminology used herein is for the purpose of describing particular embodiments and is not intended to be limiting of exemplary embodiments. As used herein, singular forms, such as "a" and "an," are intended to include the plural forms as well, unless the context indicates otherwise. Additionally, the terms, "includes," "including," "comprises" and "comprising," specify the presence of the stated elements or steps but do not preclude the presence or addition of one or more other elements or steps.

In methods for aerosol collection and fluid analysis, particulates from an aerosol sample can be collected using an aerosol-collection disk 12, as described in section A, below. The collected particulates can then be added to a dispersing fluid and dispensed via spinning from a fluid-dispensing disk 14, as described in section B, below, for analysis.

Examples of air samples that can be taken for the aerosol-collection step include air samples that may contain harmful pathogens as well as air samples from, e.g., factories, mines and ships for air-quality evaluation/monitoring. If an air sample containing a pathogen is taken, the pathogen can be collected in the aerosol-collection step and then added to the dispensing fluid 33 (e.g., a liquid). In the fluid-dispensing step, the fluid 33 containing the pathogen can be loaded into one of multiple reservoirs 32 in or on a fluid-dispensing disk 14, multiple embodiments of which are described in section B, below. By governing the rotation of the fluid-dispensing disk 14, the pathogen-containing fluid 33 can be selective dispensed from its reservoir 32 at one point in time and additional liquids can be selectively released from their respective reservoirs 32 at different times.

In one embodiment, the pathogen is collected first from the aerosol cloud via the spin-induced aerosol collection method on the disk 14; then, in a pre-wash step, a fluid 33 (e.g., a CO2i cell culture medium, which is a common off-the-shelf reagent) is released to wash off any protective coatings on the pathogen (an optional step); next, a second liquid (e.g., B-Cells suspended in the CO2i medium) is released to interact with the pathogen (e.g., tag it with a detectable marker or cause it to luminesce); a third release of the same second liquid may then be dispensed to perform a confirmation assay on the same sample of particles (optional step); a subsequent fourth delivery may be of a different strain of B-Cells engineered to detect another pathogen, allowing one collection of particles to be analyzed multiple times to detect various pathogens (optional step); and then a final, fifth dispense may be of a fluid, such as CO2i medium, to rinse the test area in preparation for the next particle collection and test sequence (optional step). Various combinations of the mentioned optional steps may be used depending on the test required including but not limited to multiple confirmation assays, confirmation assays of multiple tests per pathogen collection, selective dispensing of the pre-wash dispense, etc. The fluids 33 can be released via vector acceleration of the rotating liquid with different orientations of reservoirs 32 and release mechanisms or via differences in the radii of the reservoirs 32 on or in the fluid-dispensing disk 14, as discussed in section B.

Both the aerosol-collection disk 12 and the fluid-dispensing disk 14 are configured for mounting on a stage including a shaft 18 on a rotary motor 16 via a motor mount, such as a common motor coupling, on the shaft 18. The disks can have a diameter between about 2 inches to about 18 inches (e.g., about 4-5 inches) and a thickness, e.g., of one inch or less (e.g. about ¼" thick) The motor 16, (e.g., a 10.5 Watt Model 2842024C DC motor from FAULHABER Group, Germany) is provided with a control for varying speed of rotation and acceleration of the stage, allowing for controlled rotational velocity and acceleration of the disk 12/14, as described below. In alternative embodiments, aerosol-collection and fluid dispensing are incorporated into a single disk, with the structures for both functions incorporated into/onto a single platform.

Figure 2:
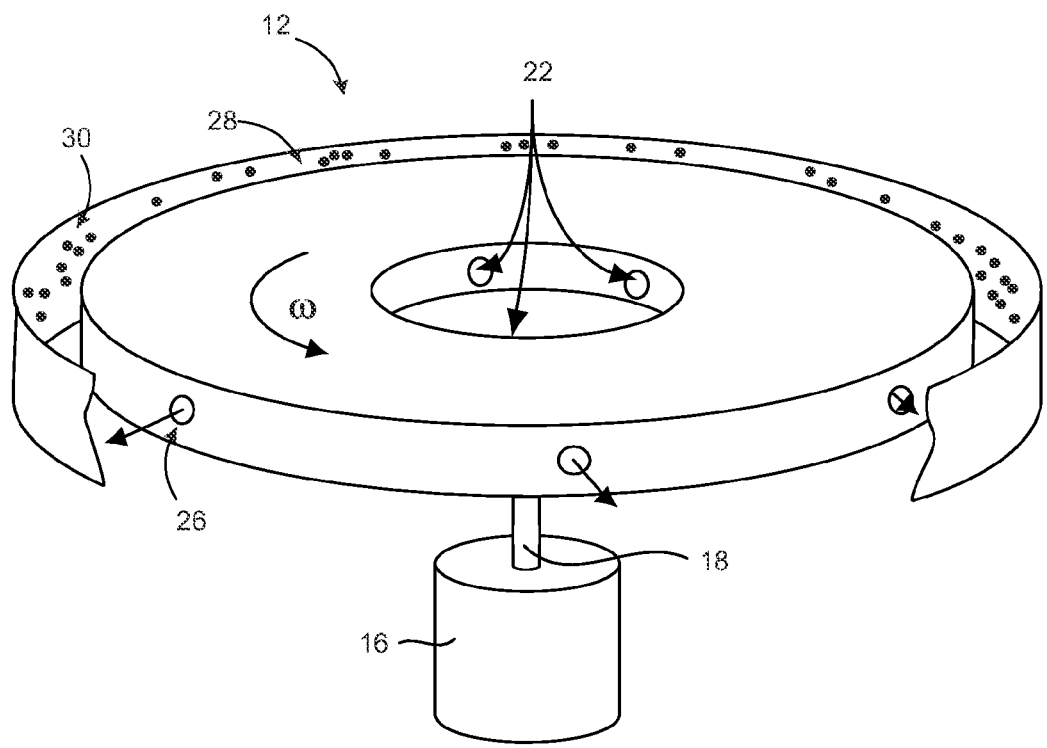
FIG. 2 shows an aerosol-collection disk spun by a motor with a particle-laden air flow entering inlets at the center of the aerosol-collection disk, exiting the disk at its perimeter and impinging on the inner surface of an annular ring co-rotating with the aerosol-collection disk.

A. Spin-Induced Aerosol Collection:

An aerosol-collection disk 12 having a hole in the center (i.e., the inlet 22), and channels 24 running radially outward to outlets 26 at the outer diameter of the aerosol-collection disk 12 is shown in FIGS. 1 and 2. When spun at an angular velocity, $\omega$, a radial flow, V, of an aerosol results due to the generated tangential flows, $V_i$ at the inlet 22 and $V_e$ at the exhaust or outlet 26. This flow can be generated entirely or almost entirely by centrifugal acceleration. The radial distance to the inlet 22 and the outlet 26 is $R_i$ and $R_e$, respectively.

The required radial flow velocity, V, may be calculated from the desired volume flow rate, Q, and the cross-sectional area, A, of the port, as follows:

$$V = Q/A, \quad (1)$$

and the resulting pressure drop, Δp, across the radial channel 24 between the inlet 22 and the outlet 26 is expressed, as follows:

$$\Delta p = p_i - p_e = 1/2 \rho V^2, \quad (2)$$

wherein $p_i$ is the pressure of the aerosol at the inlet 22, and $p_e$ is the pressure of the aerosol at the outlet 26. Variable, p, is air density. By Bernoulli's equation, the pressures and tangential velocities at the inlet 22 and outlet 26 are related, as follows:

$$p_i + 1/2 \rho V_i^2 = p_e + 1/2 \rho V_e^2, \quad (3)$$

and the tangential flows are expressed as follows:

$$V_i = \omega R_i \text{ and } V_e = \omega R_e. \quad (4)$$

Substituting Equation 1, Equation 2 and Equation 4 into Equation 3 and rearranging allows the determination of the required disk angular velocity, as follows:

$$\omega = \left( \frac{2 \Delta p}{(R_e^2 - R_i^2) \rho} \right)^{1/2}. \quad (5)$$

FIG. 2 further depicts the aerosol-collection disk 12 spun by a motor 16, with the particle-laden air flow entering the inlets 22 at the center of the disk 12. Upon exiting the aerosol-collection disk 12, the airflow makes a sudden turn, resulting in the particles 30 in the flow impinging on the inner surface of an annular-band particle collector 28 co-rotating with the disk 12. The annular band 28 can be in the form of a continuous ring or in the form of one or more segments of a ring, where at least one segment is in the vicinity of each outlet port 26.

Figure 3:
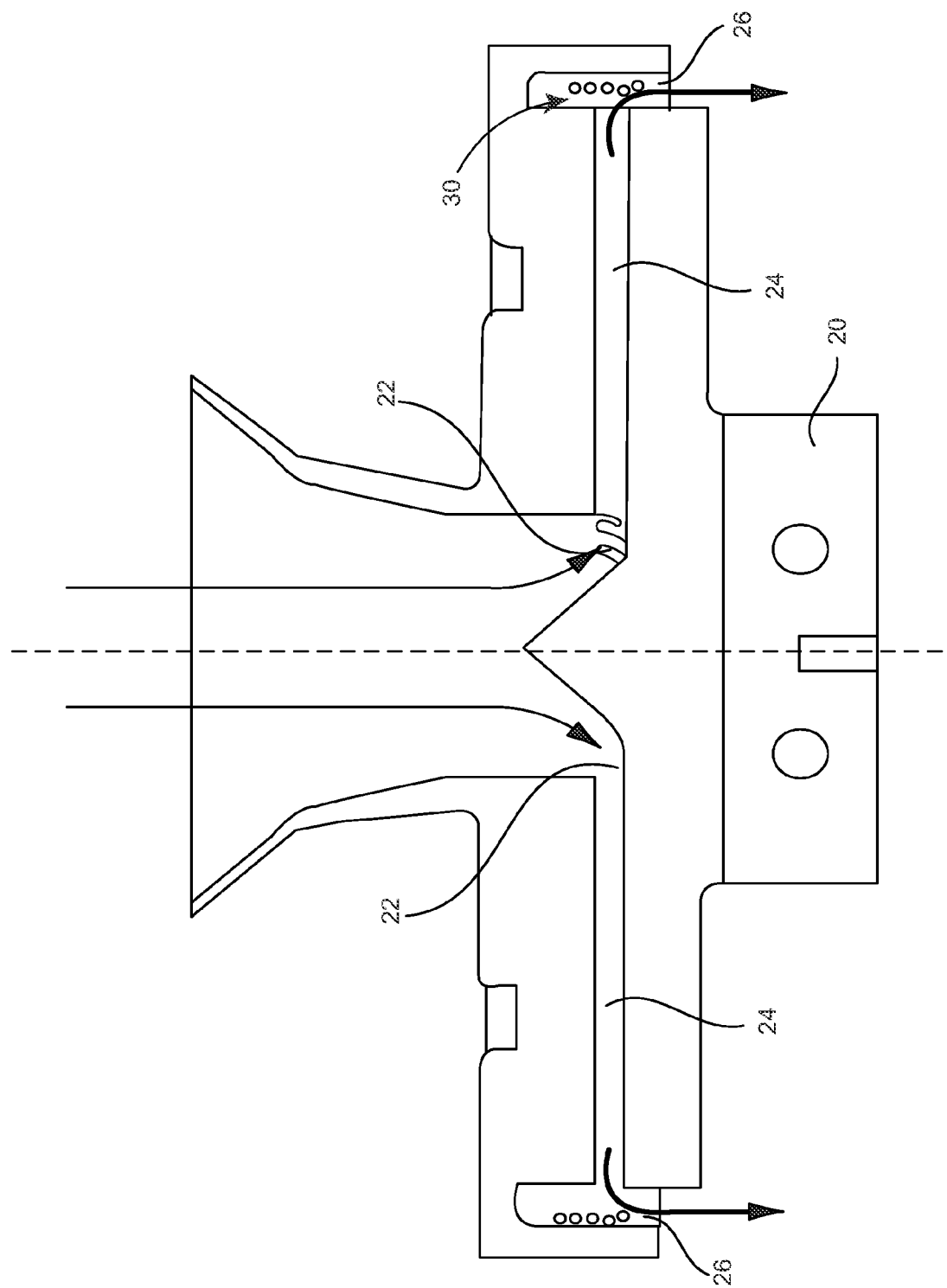
FIG. 3 is a sectional illustration of a prototype model of the aerosol-collection disk as depicted in FIG. 2.

A sectional view of a computer-aided-design model of a prototype used to quantify the aerosol-collection disk 12 is shown in FIG. 3, with aerosol flow shown with the arrows. Particles 30 from the aerosol are deposited on the inner surface of the annular-ring particle collector 28, which is connected to the spinning aerosol-collection disk 12 as the air flow makes the sharp turn to exhaust.

For an aerosol-collection disk 12 having a 0.5-inch radius to the inlet nozzle 22 and a 2-inch radius to the outlet port 26 with a 1-mm diameter, the rotation speed (expressed in revolutions per minute), for the disk 12 was computed for achieving three desired flow rates per channel (ch) in liters per minute per channel and is show in Table 1.

TABLE 1

| Flow Rate | Disk Speed |
|---|---|
| 4 l/min/ch | 2,900 RPM |
| 19 l/min/ch | 13,900 RPM |
| 30 l/min/ch | 22,800 RPM |

The lower bound of the efficiency of the spin-induced-aerosol-collection concept, relative to using a conventional blower capable of achieving similar volume flow rates, was computed based on the power of the total flow through the prototype aerosol-collection disk 12, $P_{flow}$, the rated motor maximum power, $P_{motor}$, and the published motor efficiency, $\eta_{motor}$, using the following equations:

$$P_{flow} = \left( \Delta p + \frac{1}{2} \rho V^2 \right) \sum_n v_n, \quad (6)$$

where $n=1:N_p$, and $N_p$ is the number of ports. $v_n$ is the volume flow rate through each port. The minimum bound of the efficiency of the spin-induced aerosol collection (SIAC), $\eta_{SIAC}$, can be expressed as follows:

$$\eta_{SIAC} = \frac{P_{flow}}{P_{motor}} \eta_{motor}. \quad (7)$$

The efficiency of a conventional blower attaining similar flow rates was determined by comparing measured air flow, measured using a flow meter, to the measured blower electrical power consumed. Table 2 shows that the SIAC efficiency lower bound of 51% is eight times greater than the example blower efficiency of 6%.

TABLE 2

| | Flow Rate | Pressure Drop | Electrical Power (Input) | Total Flow Power (Output) | Efficiency |
|---|---|---|---|---|---|
| SIAC | 98 l/min | 1390 Pa | 8.86 W (1) | 4.54 W | >51% (2) |
| Blower | 100 l/min | 1400 Pa | 40.3 W | 2.4 W | 6% (3) |

As indicated, above:
(1) the SIAC electrical power was the maximum motor power/motor efficiency, 6.56 W/0.74=8.86 W;
(2) the actual input power is unknown and thus efficiency may be higher than 51%; and
(3) the best measured blower efficiency was 14%.

Additional benefits of the SIAC concept over using a conventional blower are reduced volume, reduced weight and less cooling due to higher efficiency.

Figure 4:
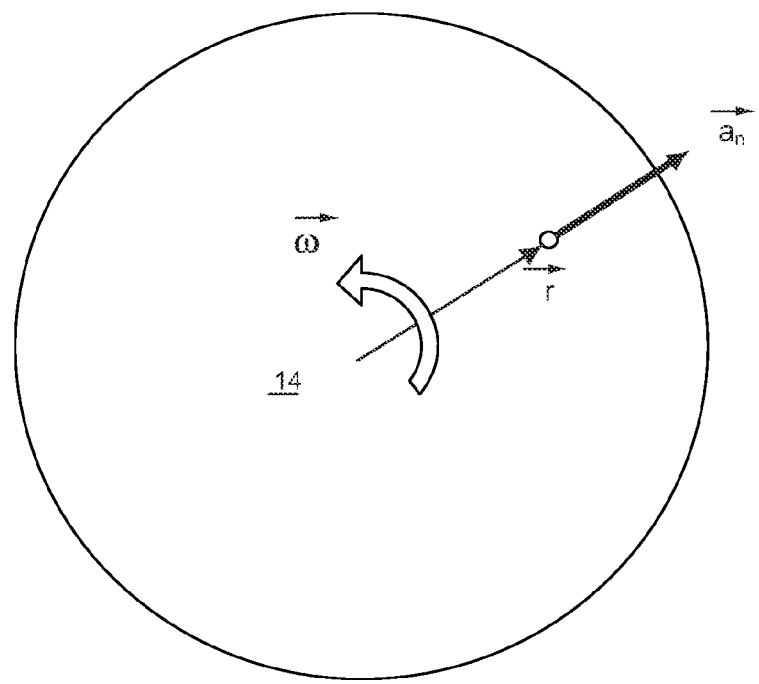
FIG. 4 depicts acceleration of a point on a fluid-dispensing disk rotating with constant angular velocity.

B. Spin-Induced Fluid Dispensing i) Sequential Constant-Velocity Dispensing of Fluids A point on a fluid-dispensing disk 14 at radius, r, with constant angular velocity, ω, sees a radially outward acceleration, $a_n = r\omega$, as shown in FIG. 4.

Figure 5:
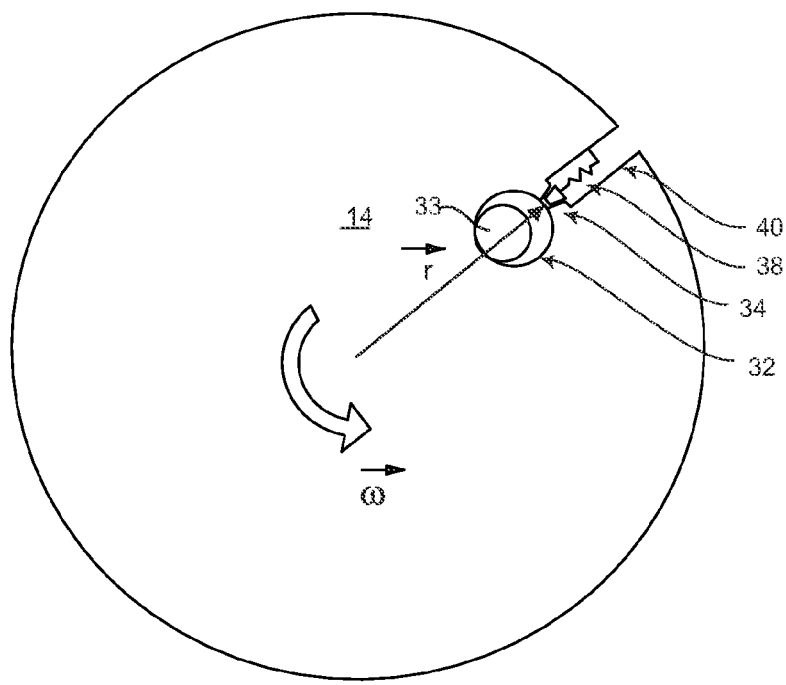
FIG. 5 shows a plunger sealing a reservoir on a fluid-dispensing disk.
Figure 6:
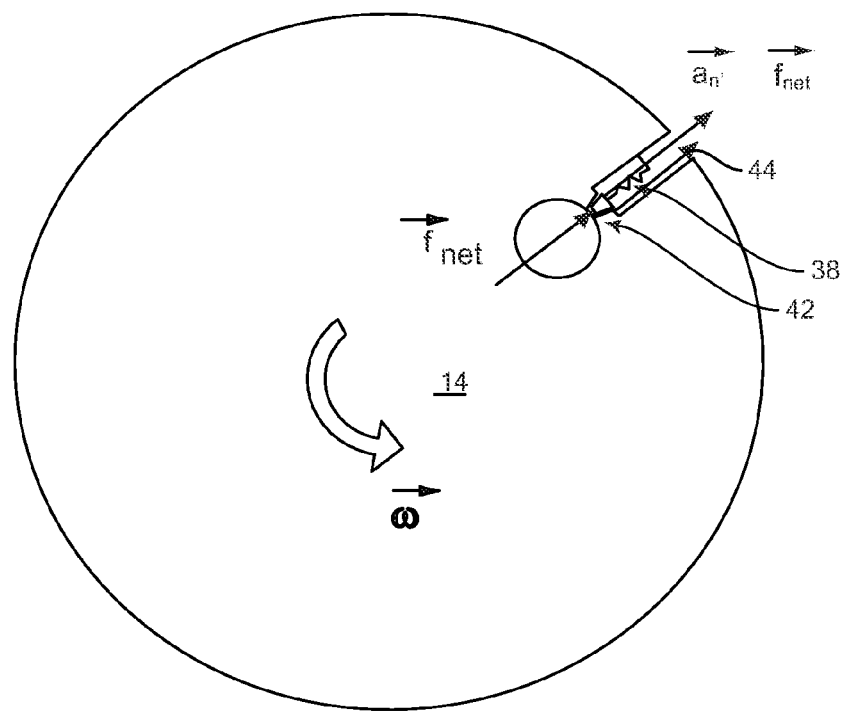
FIG. 6 depicts the plunger removed from the gate of FIG. 5 to allow fluid to dispense.

Considering the point on the disk 14 to be the location of a plunger 34, the plunger 34, which is loaded by a spring 38, may be used to seal a reservoir 32 containing fluid 33, as shown in FIG. 5. The force due to normal acceleration of the plunger 34 is simply the mass of the plunger 34, $m_p$, times $a_n$ or $f_p = m_p a_n = m_p(r\omega)$. When the net force, $f_n$, acting on the plunger 34 is greater than and in the opposite direction to the net force due to the spring 38 and other resistive forces, such as stiction (static friction), mechanical detent, and inertia, the spring 38 compresses and the plunger 34 moves radially outward, opening the outlet gate 42 and allowing the fluid to dispense 44, as shown in FIG. 6. In other embodiments, the plunger 34 can be held in the outlet gate 42 not by a spring 38 but instead by another mechanism, such as a detent or a strip of breakable material, such as tape, that will rip away at a prescribed angular velocity or force vector.

Figure 7:
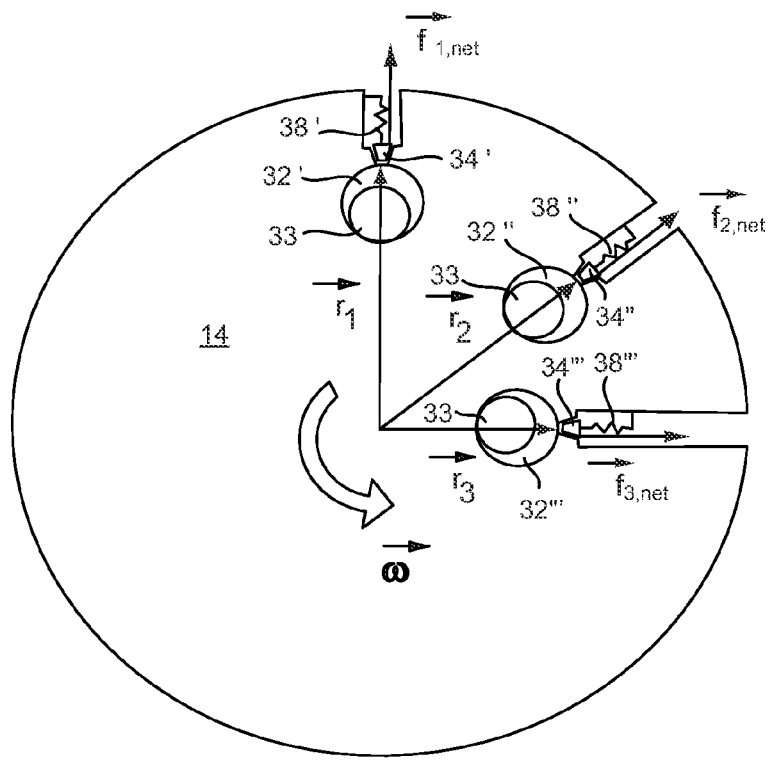
FIG. 7 illustrates multiple reservoirs at different radii on a fluid-dispensing disk for sequential dispensing of fluids using mechanical valves.

FIG. 7 shows a fluid-dispensing disk 14 with three reservoirs 32, each at different distances from the spin center (e.g., with a difference beyond normal machining tolerances, such as a difference in radius of at least 5% or 10% between each reservoir). For the case shown, each reservoir 32 is sealed using identical plungers 34 and spring stiffness such that the force required to open each is similar. The plungers 34 for each reservoir 32 are located at radii, $r_1$, $r_2$, and $r_3$, where $r_1 > r_2 > r_3$, as shown. For a given angular velocity, $\omega$, the normal acceleration at each of the three plungers 34 is $a_{n1} > a_{n2} > a_n$, thus the forces due to normal acceleration acting on the plungers 34 are then $f_1 > f_2 > f_3$, having respective net forces, after subtracting out the forces resisting plunger motion, of $f_{1,net} > f_{2,net} > f_{3,net}$.

At the critical angular velocity, $\omega_1$, the net force $f_{1,net}$ acting on the plunger 34' sealing the first reservoir 32' is greater than the resting force due to the stiffness of the spring 38 and other resistive forces, such as stiction, of the plunger 34, resulting in the plunger 34' moving radially outward, dispensing the fluid 33 from the reservoir 32'. Since the critical angular velocities of the remaining reservoirs 32" and 32''' are greater than $\omega_1$ (i.e., $\omega_3 > \omega_2 > \omega_1$), and the plungers 34" and 34''' at the second and third reservoirs 32" and 32''' remain intact, sealing their respective reservoirs 32. Increasing the angular velocity to $\omega_2$, the plunger 34" moves radially outward, dispensing fluid 33 from the second reservoir 32" while keeping the plunger 34''' sealing the third reservoir 32''' intact. Further increasing the angular velocity to $\omega_3$ results in the remaining third plunger 34''' moving radially outward, dispensing the fluid 33 from the third reservoir 32'''.

Figure 8:
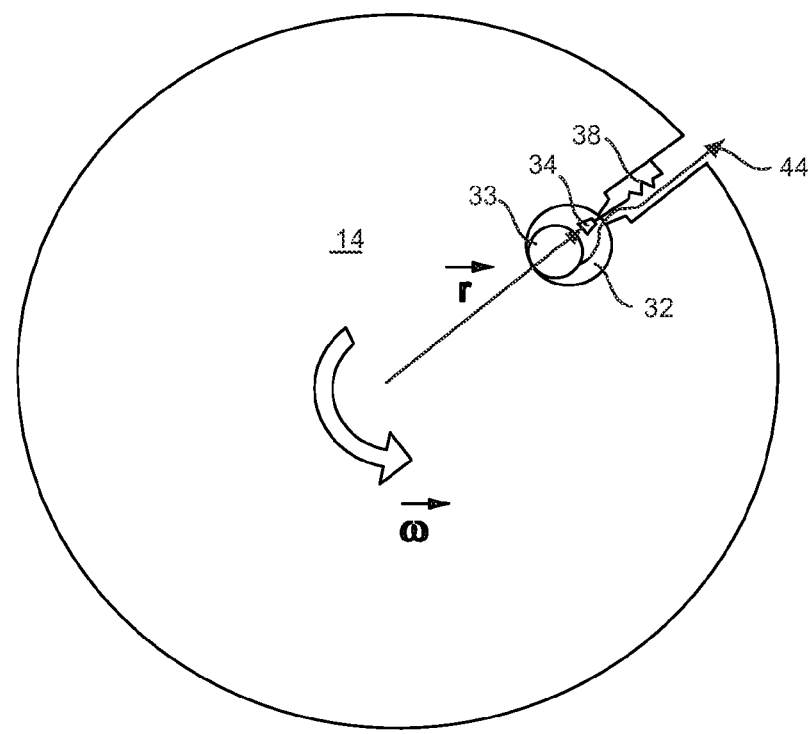
FIG. 8 shows a gate with a plunger in a "normally open" configuration on a fluid-dispensing disk.

This concept may also be used to stop a fluid from flowing. As shown in FIG. 8, the plunger 34 is designed in a "normally open" configuration, allowing fluid 33 to flow through the gate 42 for angular velocities less than the critical velocity, $\omega_1$. The fluid 33 may originate in a reservoir 32 located in or on the fluid-dispensing disk 14, as shown, or may originate outside the disk 14 and be passing through it via a flow-through channel.

Figure 9:
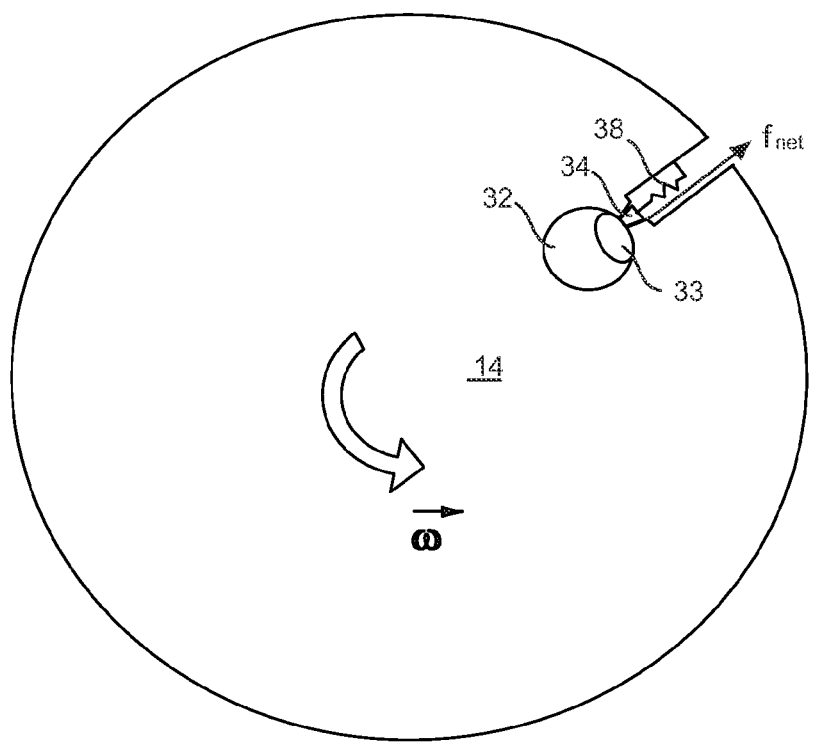
FIG. 9 depicts the gate of the "normally open" configuration in a closed position.

As $\omega \to \omega_1$, the net force acting on the plunger 34, $f_{net}$, is greater than the sum of resistive forces inhibiting plunger motion allowing the plunger 34 to move and seal the gate 42, thus preventing further flow of the fluid 33, as shown in FIG. 9.

Without the benefit of a mechanical latch securing the plunger 34 in the closed position, the fluid 33 may be allowed to flow by decreasing the angular velocity, $\omega$, to below the critical angular velocity. However, the use of a mechanical latch securing the plunger 34 may be used to prevent flow from recurring after slowing from the critical angular velocity.

Figure 10:
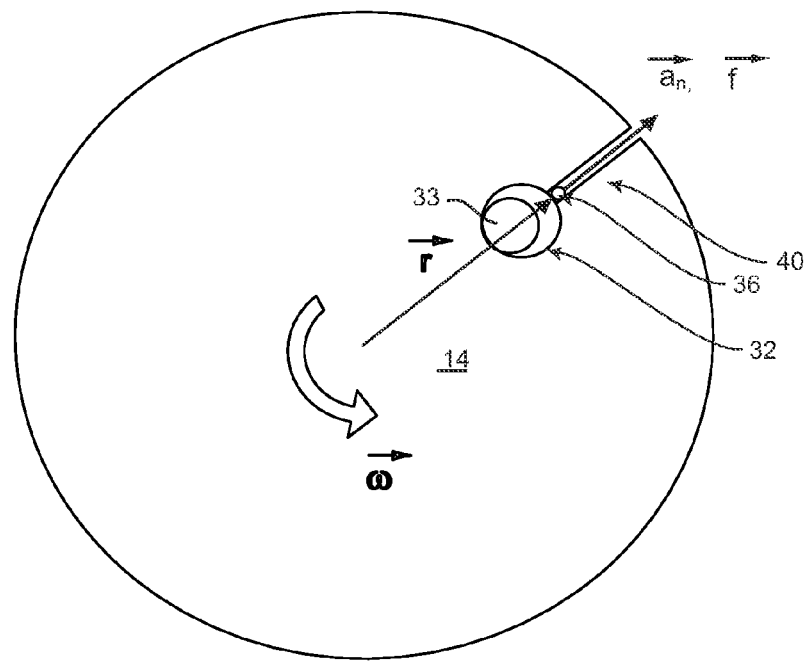
FIG. 10 shows a viscous plug subjected to constant angular velocity on a fluid dispensing disk.

In other embodiments, a viscous plug 36 is used in place of the plunger 34, wherein the viscous plug 36 is used to seal a reservoir 32 containing fluid 33, as shown in FIG. 10. The viscous plug 36, upon achieving a minimum angular velocity, is ejected due to the resulting normal acceleration, $a_n$, acting on it such that the shear force acting on the viscous plug at the wall is overcome by the body force acting on the viscous plug. The normal acceleration, $a_n$, required to dispense the viscous plug is expressed as follows:

$$a_n \geq \frac{2\tau_w(w+h)}{\rho w h}, \tag{8}$$

where $\tau_w$ is the shear force of the viscous plug, having density $\rho$, acting at the wall of the duct of width, w and height, h.

Figure 11:
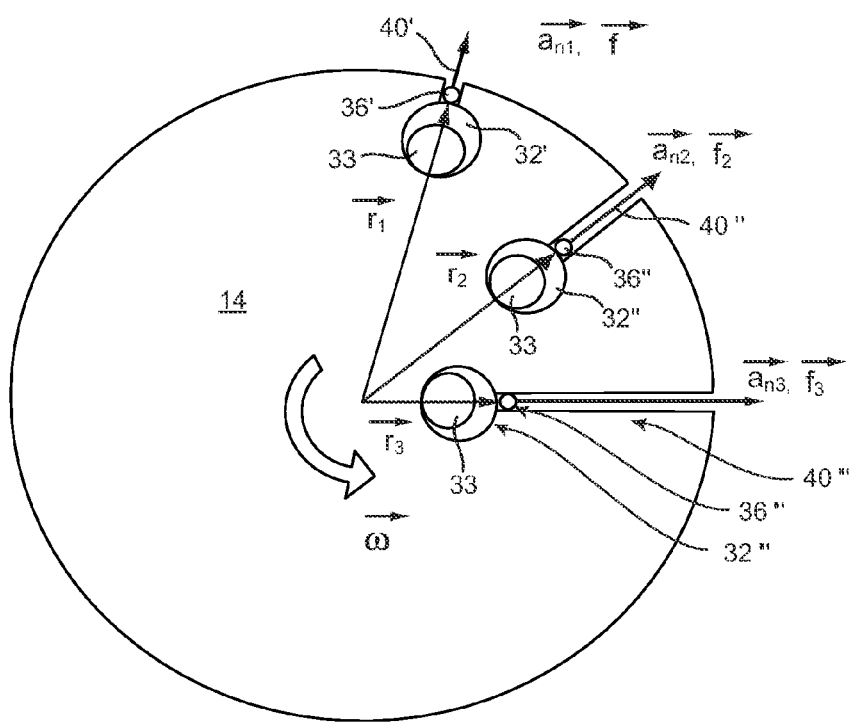
FIG. 11 illustrates multiple reservoirs with viscous plugs at different radii on a fluid-dispensing disk for sequential dispensing of fluids.

A fluid-dispensing disk 14 with three reservoirs 32, each at different distances from the spin center is shown in FIG. 11. The viscous plugs 36 for each reservoir 32 are located at radii, $r_1$, $r_2$, and $r_3$, where $r_1 > r_2 > r_3$, as shown. For a given angular velocity, $\omega$ (i.e., $a_{n1} > a_{n2} > a_{n3}$); thus, the forces due to normal acceleration acting on the viscous plugs 36 are then $f_1 > f_2 > f_3$. At the critical angular velocity, $\omega_1$, the net force, $f_1$, acting on the viscous plug 36' sealing the first reservoir 32' is sufficiently large to overcome any resistive forces keeping the viscous plug 36' in place; and, thus, the viscous plug 36' is ejected from the gate, dispensing the fluid 33 from the first reservoir 32'. Since the critical angular velocities of the remaining reservoirs 32" and 32''' are greater than $\omega_1$, $\omega_3 > \omega_2 > \omega_1$, the viscous plugs 36" and 36''' at the second and third reservoirs 32" and 32''' remain intact. Increasing the angular velocity to $\omega_2$ ejects the viscous plug 36" and fluid 33 from the second reservoir 32" while keeping the viscous plug 36''' sealing the third reservoir 32''' intact. Further increasing the angular velocity to $\omega_3$ ejects the remaining third viscous plug 36''', dispensing the fluid 33 from the third reservoir 32'''.

ii) Spin-Vectored Dispensing of Fluids

Figure 12:
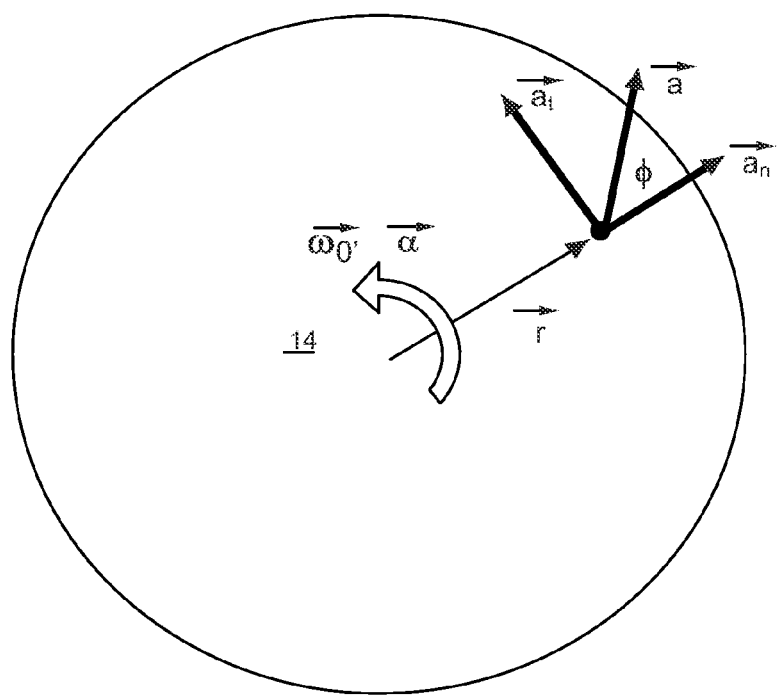
FIG. 12 depicts the acceleration components of a point on a rotating fluid-dispensing disk due to a disk having some prescribed angular velocity and angular acceleration.

A point on a fluid-dispensing disk 14 at a radius, r, having an initial angular velocity, $\omega_0$, and angular acceleration, $\alpha$, is subject to the acceleration vectors shown in FIG. 12, where the normal acceleration, $a_n$, can be expressed as follows:

$$\vec{a}_n = \vec{r}(\omega_0 + \alpha t)^2 \vec{e}_n, \tag{9}$$

where t is time, and $e_n$ is the unit vector describing the direction of the radial or normal acceleration; and the tangential acceleration, $a_t$, can be expressed as follows:

$$\vec{a}_t = \vec{r}\alpha \vec{e}_t \tag{10}$$

where $e_t$ is the unit vector describing the direction of the tangential acceleration having an acceleration magnitude, $$|a| = \sqrt{(a_n^2 + a_t^2)}, \tag{11}$$

and an acceleration vector angle, $$\phi = \tan^{-1}\left(\frac{a}{(\omega_0 + a)^2}\right). \tag{12}$$

Figure 13:
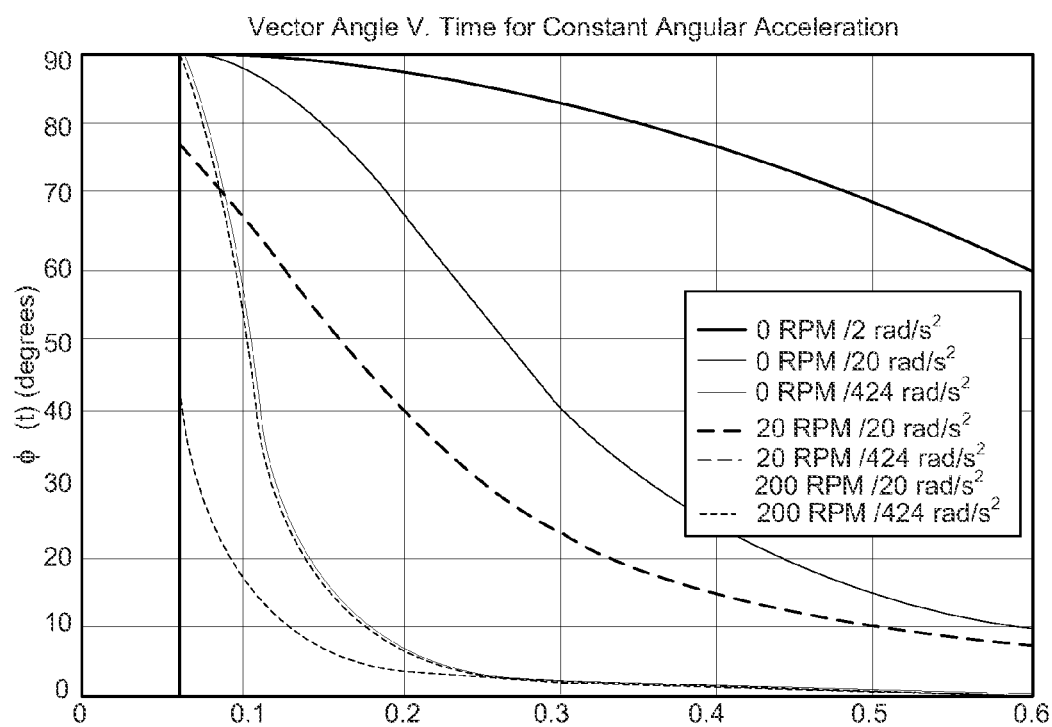
FIG. 13 provides a series of plots of vector angle, $\phi$ as shown in FIG. 12 versus time for different combinations of (a) initial angular velocity and (b) angular acceleration.

FIG. 13 shows variation in vector angle over time, $\phi(t)$, due to increasing angular velocity, $\omega$, of the disk 14 due to constant angular acceleration, $\alpha$, for an ideal (instant on) motor 16 starting from three different initial angular velocities $\omega_0$ (0 RPM, 20 RPM, and 200 RPM). All accelerations shown are positive and begin at t=0.5 seconds. Acceleration due to an actual motor 16 will have a ramp-up of acceleration, thereby resulting in an initial increasing vector angle, $\phi$. For continuing acceleration, the vector angle, $\phi$, approaches the normal ($\phi \to 0$) as per equation 12 for increasing time as the angular velocity (see equation 9, $\alpha t$) increases.

The vector angle, $\phi$, depends on (a) initial spin rate, $\omega_0$; (b) angular acceleration, $\alpha$; and (c) duration of the applied angular acceleration, t. For the curves shown in FIG. 13, solid lines show the vector angle, $\phi$, versus time, t, starting with the motor 16 at zero initial angular velocity, $\omega_0 = 0$ RPM. Dashed lines have $\omega_0 = 20$ RPM and dot-dash lines are for $\omega_0 = 200$ RPM. The largest vector angles, $\phi$, are for large angular acceleration, $\alpha$, with an initial angular velocity, $\omega_0 = 0$.

Figure 14:
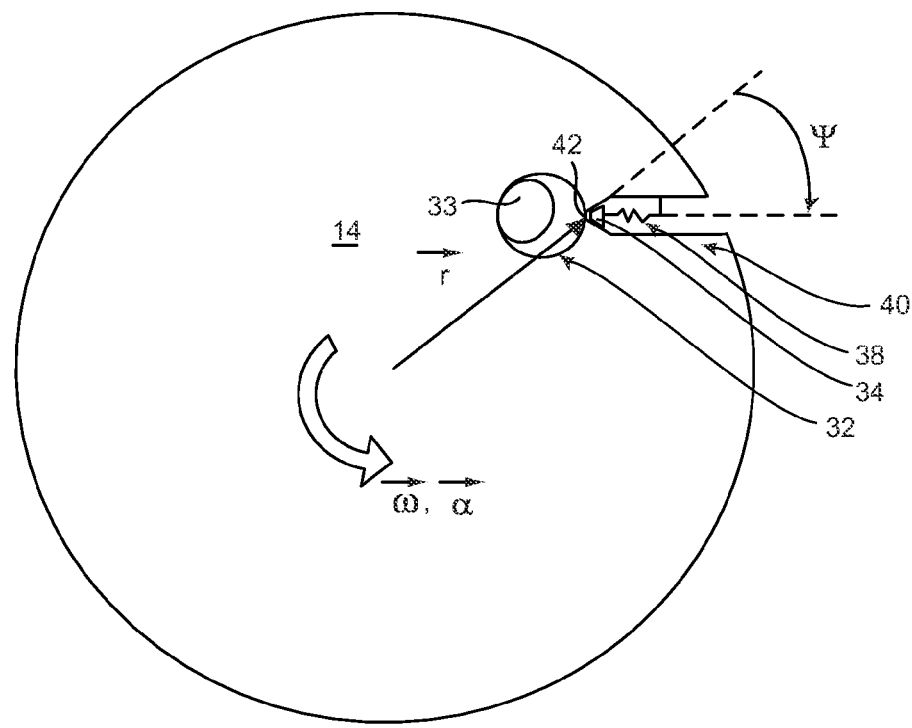
FIG. 14 depicts a reservoir oriented on a fluid-dispensing disk with a gate and plunger sealing the reservoir at angle $\psi$ from the radius of the reservoir.

The fluid-dispensing disk 14 in this embodiment takes advantage of the ability to vector the net acceleration acting at a point on the accelerating disk 14 by pulsing the angular velocity of the disk 14. The point on the disk 14 where we consider the vectored acceleration is the location of a plunger 34 loaded by a spring 38 anchored to the disk 14, wherein the plunger 34 acts as a stopper to seal a reservoir 32 containing fluid 33; the plunger 34 may be located at the end of a flow-through channel extending from the reservoir 32 at the gate 42 of a runner 40 and oriented at an angle, $\psi$, to the radius, as shown in FIG. 14, or the reservoir can be in the form of a flow-through channel through which the fluid is supplied.

Figure 15:
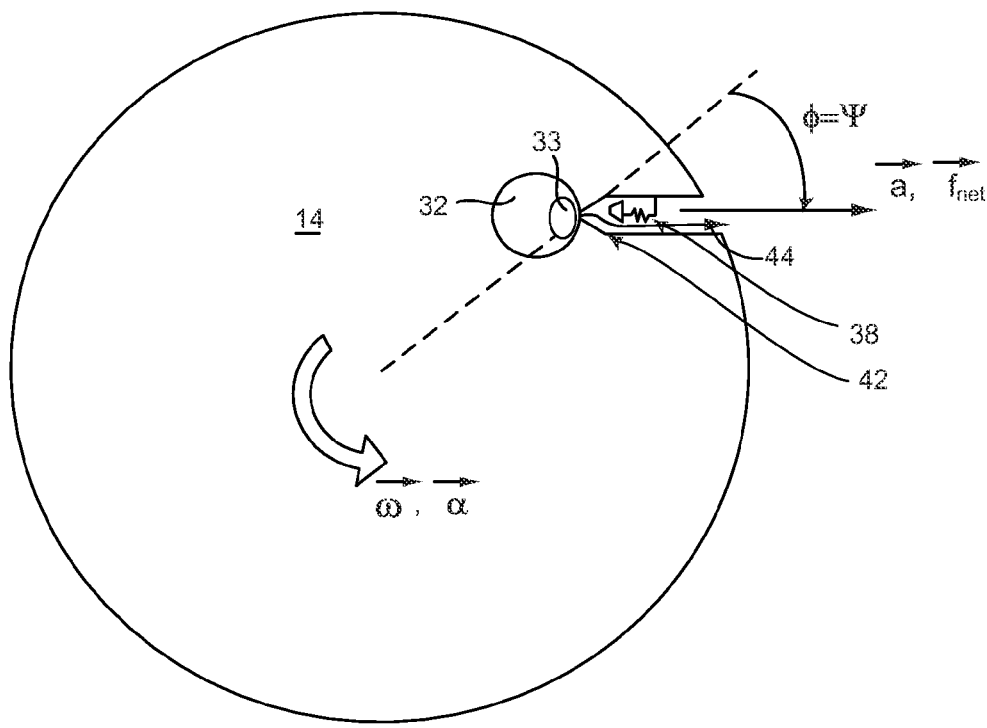
FIG. 15 shows a plunger subjected to vectored acceleration on a fluid-dispensing disk allowing the fluid in the reservoir to dispense.

Applying angular acceleration, α, to the fluid-dispensing disk 14, the acceleration acting on the plunger 34 may be vectored to some angle, φ. The force due to acceleration of the plunger 34 is simply the mass of the plunger 34 times the acceleration magnitude, a, or $f_p = m_p a$. Orienting the acceleration vector such that φ→ψ, as shown in FIG. 15, aligns the force vector, $f_{net}$, to coincide with the angle along which the runner is aligned, compressing the spring 38 to displace the plunger 34 from the gate 42 to break the seal to the reservoir 32, allowing the fluid 33 to dispense there from, as shown by arrow 44.

Figure 16:
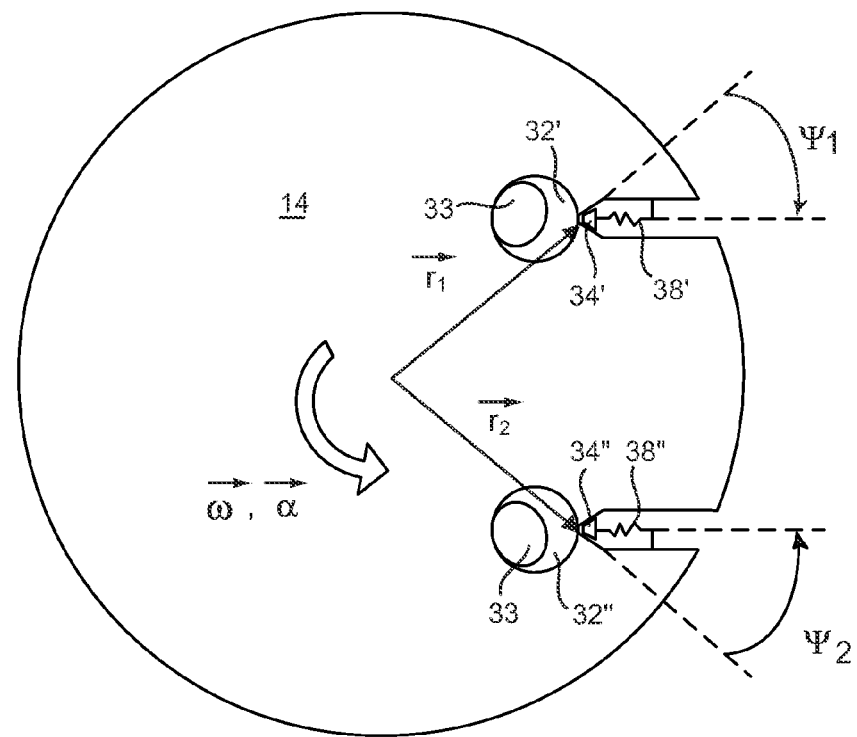
FIG. 16 depicts multiple reservoirs sealed with plungers oriented at different angles on a fluid-dispensing disk for spin-vectored dispensing of a fluid.
Figure 17:
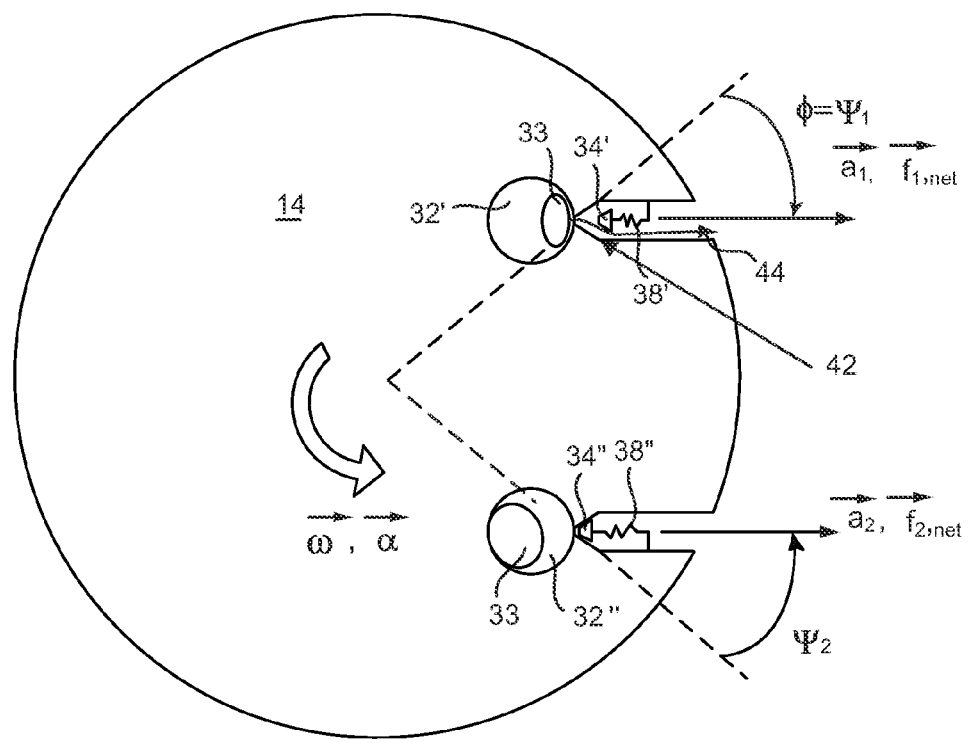
FIG. 17 depicts spin vectoring to dispense fluid from one of the reservoirs shown in FIG. 16.

A fluid-dispensing disk 14 with two reservoirs 32 is shown in FIG. 16. Each reservoir 32 has the same design but is oriented with its gate 42 at a different angle, $\psi_1$, $\psi_2$, to the radius, r (e.g., with the orientation angle differing by at least 5° or 10°). For this example, the plunger 34 for each reservoir 32 is at the same radial distance, r, from the center. Applying angular acceleration, $\alpha_1$, to the disk 14 such that $\phi_1 \to \psi_1$ compresses the spring 38' to displace the plunger 34' and consequently dispenses the corresponding fluid 33 from the first reservoir 32' in the form of an exiting flow 44, as shown in FIG. 17, while keeping the second reservoir 32" sealed and its fluid 33 contained and intact. Fluid 33 in the second reservoir 32" may then be dispensed by applying $\alpha_2$, such that $\phi_2 \to \psi_2$, thereby compressing spring 38" and retracting plunger 34".

Figure 18:
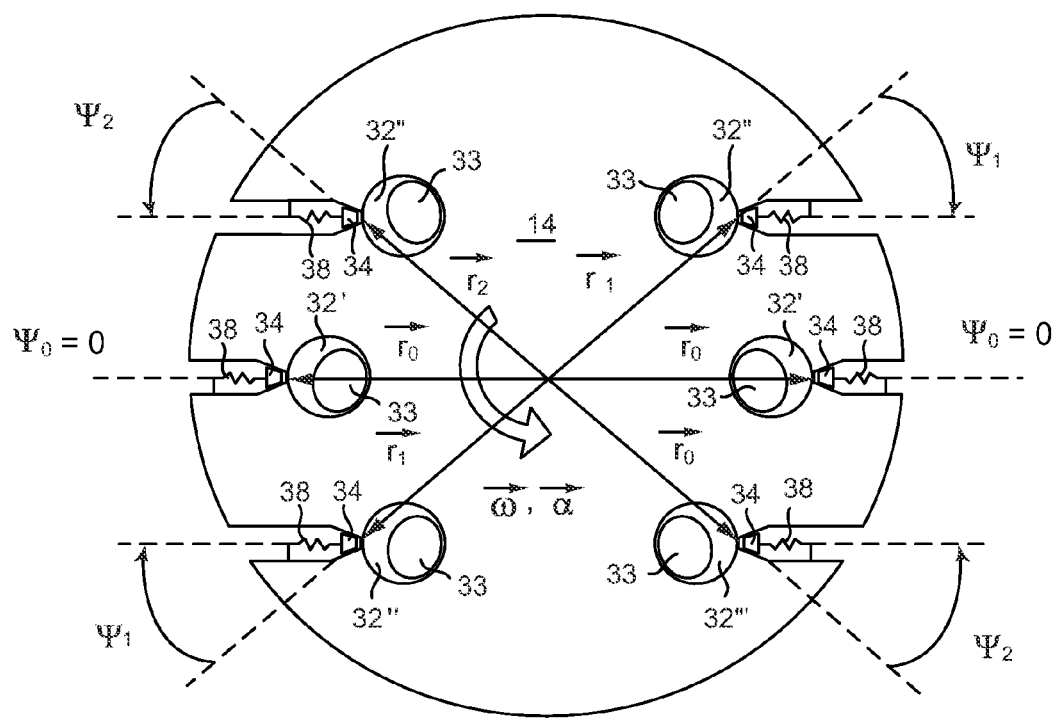
FIG. 18 illustrates another embodiment of multiple reservoirs with plungers on a fluid-dispensing disk for spin vectoring.

This process may be repeated for multiple reservoirs 32 having different gate/runner angles, $\psi_i$, as shown in FIG. 18, where multiple reservoirs 32 having similar geometries and gate/runner orientation may be combined, as shown. Here, several reservoirs 32 may be dispensed simultaneously, while the remaining reservoirs 32 remain intact. For example, three pairs of reservoirs 32 are shown having three different runner angles, $\psi_1$, $\psi_2$ and $\psi_0$, (the angle of each respective pair differing, e.g., by at least 10° from the other pairs) where the pair of $\psi_0$ reservoirs 32' are oriented in line with the radius allowing for dispensing of both simultaneously using the constant-angular-velocity method. Each remaining reservoir pair 32" and 32''' with $\psi_1$ and $\psi_2$, respectively, may be dispensed simultaneously using spin vectoring.

In addition to gate/runner angles, tailoring of the dispensing conditions may be achieved by also changing the radial distance of the plunger 34, the viscosity of the viscous plug 36 (in the case of a viscous plug) and/or the geometry of the gate 42 holding the plunger 34. Various combinations of gate/runner angles, radii, spring stiffness, plunger mass, friction, etc., may be used to achieve the desired dispensing characteristics of the fluid-dispensing disk 14.

In these embodiments, the process is shown for fluids originating in the spinning fluid-dispensing disk 14; however, the method may also be used to regulate fluid flow through the fluid-dispensing disk 14 given fluids originating outside of it and fed through a flow-through channel in the fluid-dispensing disk 14.

Figure 19:
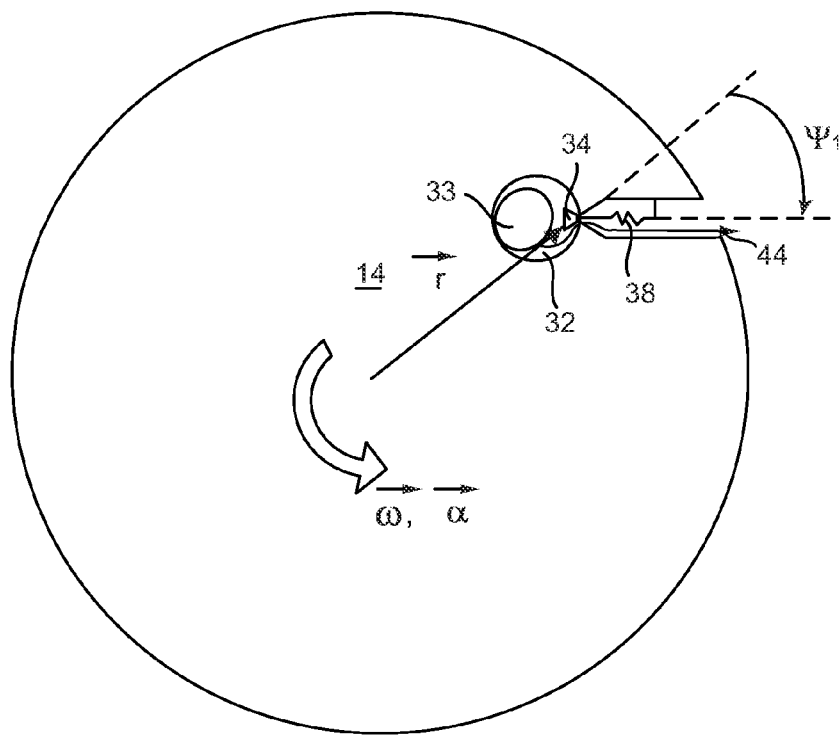
FIG. 19 shows a "normally open" gate configuration for use with spin vectoring.
Figure 20:
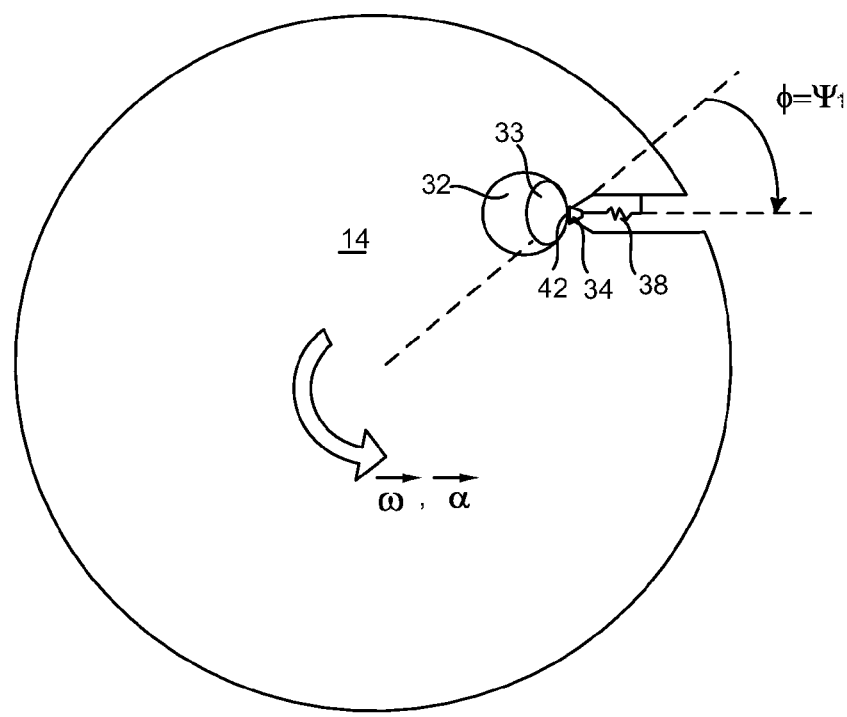
FIG. 20 shows the "normally open" gate configuration of FIG. 19 in closed position.

This concept may also be used to stop a fluid from flowing. As shown in FIG. 19, the plunger 34 is designed in a "normally open" configuration, allowing fluid 33 to flow through the gate 42. Upon reaching a critical linear acceleration acting on the plunger 34 via spin vectoring, the plunger 34 moves outward sealing the gate 42 and restricting the flow of fluid 33, as shown in FIG. 20.

Without the benefit of a mechanical latch securing the plunger 34 in the closed position, the fluid 33 may be allowed to flow by reducing the angular acceleration to below the critical angular acceleration. However, the use of a mechanical latch securing the plunger 34 may be used to prevent flow from recurring after reducing the angular acceleration below the critical angular acceleration.

Figure 21:
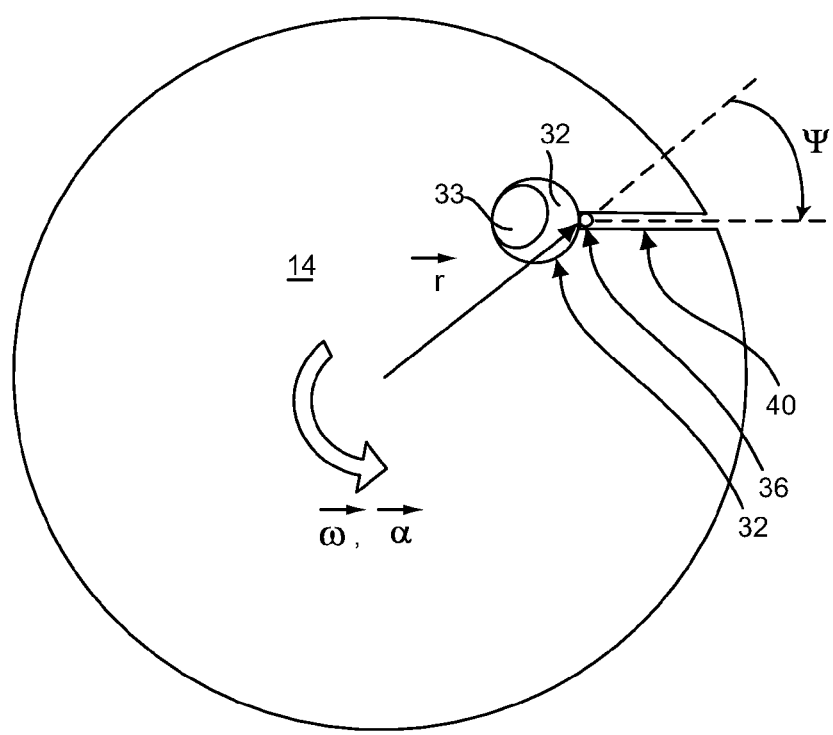
FIG. 21 depicts a reservoir oriented on a fluid-dispensing disk with a gate and viscous plug at angle $\psi$ from the radius of the reservoir.
Figure 22:
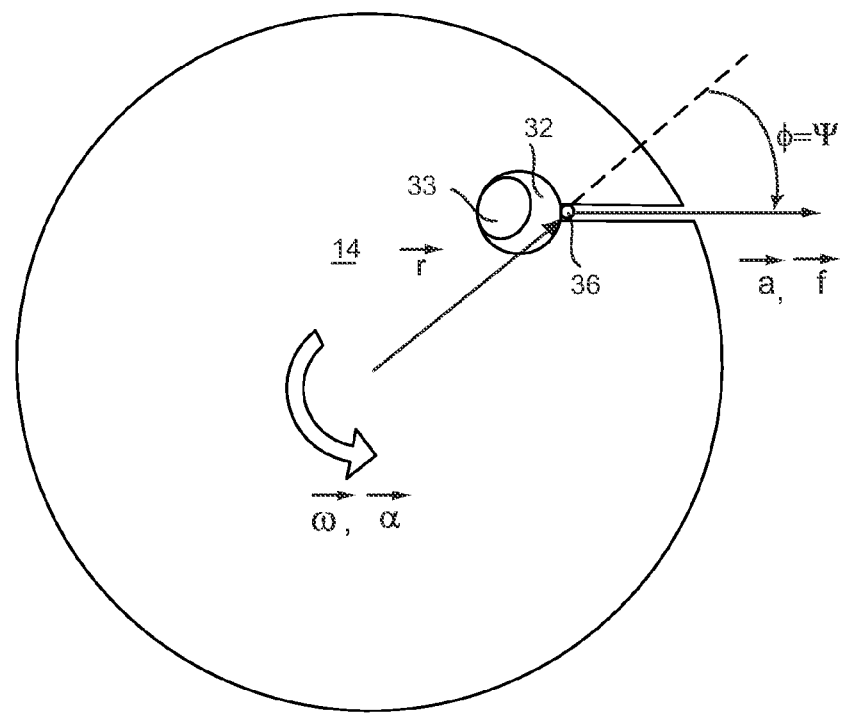
FIG. 22 shows a viscous plug subjected to vectored acceleration on a fluid-dispensing disk.

In an alternative embodiment of the fluid-dispensing disk 14, the plunger 34 of the preceding embodiments is replaced with a viscous plug 36 [e.g., formed of grease or petroleum jelly (such as VASELINE petroleum jelly produced by Unilever)], as shown in FIG. 21. As in the above-described embodiments that include a plunger 34, applying angular acceleration to the fluid-dispensing disk 14 vectors the acceleration acting on the viscous plug 36 to some angle, φ, where the force, $f_p$, due to acceleration, a, of the viscous plug 36 is simply the mass, $m_p$, of the viscous plug 36 times the acceleration magnitude, a, or $f = m_p a$. Orienting the acceleration vector such that φ→ψ, as shown in FIG. 22, aligns the force vector to the runner angle to allow the viscous plug 36 to flow, breaking the seal to the reservoir 32 and allowing the fluid 33 to dispense.

Figure 23:
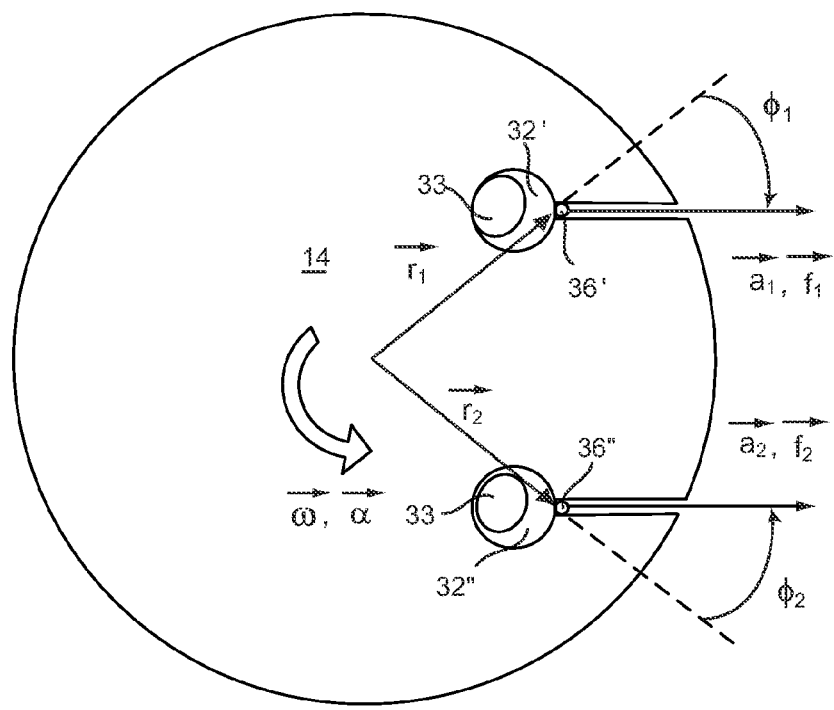
FIG. 23 depicts multiple reservoirs with viscous plugs oriented at different angles on a fluid-dispensing disk for spin-vectored dispensing of a fluid.

A fluid-dispensing disk 14 with two reservoirs 32 and viscous plugs 36 is shown in FIG. 23. Each reservoir 32 has the same design but is oriented at a different angle, $\psi_1$, $\psi_2$, to the radius (e.g., differing by at least 5° or 10°). For this example, the viscous plug 36 for each reservoir 32 is at the same radial distance from the center. Applying angular acceleration, $\alpha_1$, to the disk 14 such that $\phi_1 \to \psi_1$ displaces the first viscous plug 36' and dispenses the fluid 33 from the first reservoir 32' while keeping the second reservoir 32" sealed. Fluid 33 in the second reservoir 32" may then be dispensed by applying $\alpha_2$, such that $\phi_2 \to \psi_2$, thereby releasing the second viscous plug 36". This process may be repeated for multiple reservoirs 32 having different gate/runner angles, $\psi_i$.

Figure 24:
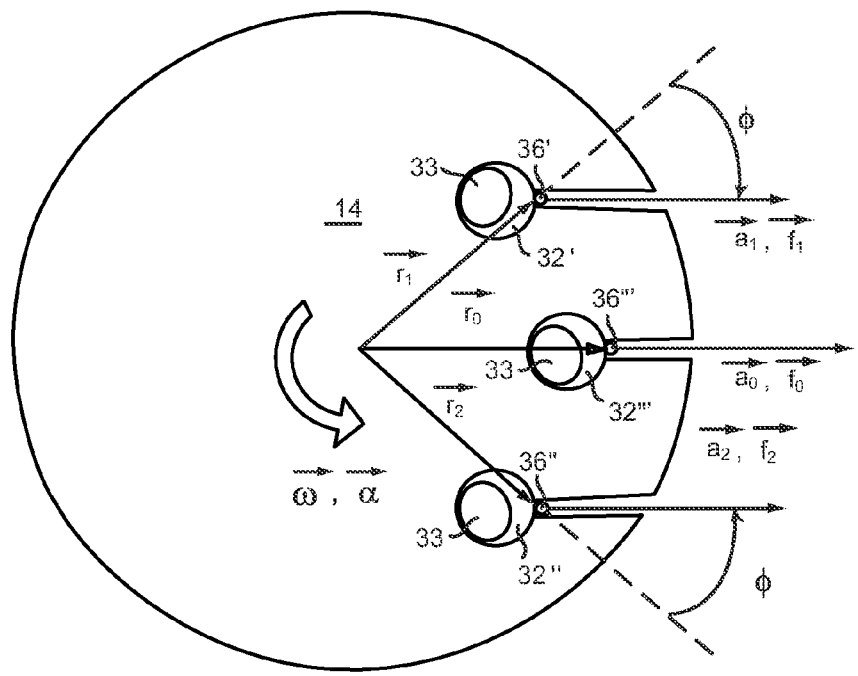
FIG. 24 shows a combination of two vectored reservoir-plug configurations with a non-vectored reservoir-plug configuration.

FIG. 24 shows the same configuration as seen in FIG. 15 with an additional reservoir 32''' oriented at ψ=0°. For this configuration, depending on the gate/runner orientation, the ψ=0° reservoir 32''' may be dispensed at constant angular velocity and the two remaining reservoirs 32' and 32" may be dispensed by spin vectoring.

Figure 25:
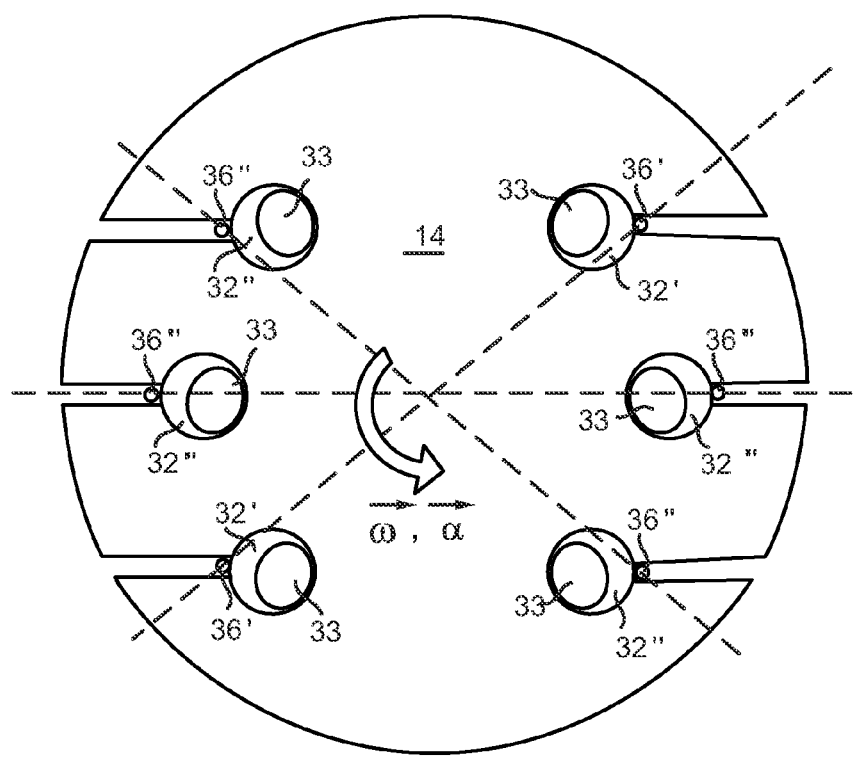
FIG. 25 illustrates another embodiment of multiple reservoirs with viscous plugs on a fluid-dispensing disk for spin vectoring.

Multiple reservoirs 32 having similar geometries and gate/runner orientation may be combined, as shown in FIG. 25. Here, several reservoirs 32 may be dispensed simultaneously while the remaining reservoirs 32 remain intact.

In addition to gate/runner angles, tailoring of the dispense conditions may be achieved by also changing the radial distance of the viscous plug 36, the viscosity of the viscous plug 36 and/or the geometry of the gate holding the viscous plug 36. Various combinations of gate/runner angles, radii, etc., may be used to achieve the desired dispensing characteristics of the disk 14.

In describing embodiments of the invention, specific terminology is used for the sake of clarity. For the purpose of description, specific terms are intended to at least include technical and functional equivalents that operate in a similar manner to accomplish a similar result. Additionally, in some instances where a particular embodiment of the invention includes a plurality of system elements or method steps, those elements or steps may be replaced with a single element or step; likewise, a single element or step may be replaced with a plurality of elements or steps that serve the same purpose. Further, where parameters for various properties are specified herein for embodiments of the invention, those parameters can be adjusted up or down by $1/100^{th}$, $1/50^{th}$, $1/20^{th}$, $1/10^{th}$, $1/5^{th}$, $1/3^{rd}$, $1/2$, $2/3^{rd}$, $3/4^{th}$, $4/5^{th}$, $9/10^{th}$, $19/20^{th}$, $49/50^{th}$, $99/100^{th}$, etc. (or up by a factor of 1, 2, 3, 4, 5, 6, 8, 10, 20, 50, 100, etc.), or by rounded-off approximations thereof, unless otherwise specified. Moreover, while this invention has been shown and described with references to particular embodiments thereof, those skilled in the art will understand that various substitutions and alterations in form and details may be made therein without departing from the scope of the invention. Further still, other aspects, functions and advantages are also within the scope of the invention; and all embodiments of the invention need not necessarily achieve all of the advantages or possess all of the characteristics described above. Additionally, steps, elements and features discussed herein in connection with one embodiment can likewise be used in conjunction with other embodiments. The contents of references, including reference texts, journal articles, patents, patent applications, etc., cited throughout the text are hereby incorporated by reference in their entirety; and appropriate components, steps, and characterizations from these references optionally may or may not be included in embodiments of this invention. Still further, the components and steps identified in the Background section are integral to this disclosure and can be used in conjunction with or substituted for components and steps described elsewhere in the disclosure within the scope of the invention. In method claims, where stages are recited in a particular order—with or without sequenced prefacing characters added for ease of reference—the stages are not to be interpreted as being temporally limited to the order in which they are recited unless otherwise specified or implied by the terms and phrasing.

What is claimed is:

1. An apparatus for aerosol collection and fluid analysis, comprising:

a rotary motor including a stage configured for rotation;

an aerosol-collection disk including at least one interior inlet, at least one peripheral outlet and a passage coupling the interior inlet with the peripheral outlet, and a particle collector opposite the peripheral outlet, wherein the collection disk is configured for mounting on the stage of the rotary motor for rotation thereon;

a fluid-analysis disk configured for mounting on the stage of the rotary motor for rotation thereon, the fluid-analysis disk comprising at least one fluid in each of a first reservoir and a second reservoir on or in the fluid-analysis disk and offset from a central axis of the fluid-analysis disk, wherein each reservoir has an outlet and a stopper in the outlet of each reservoir to seal the reservoirs, wherein selection between release of fluids from the first and second reservoirs is determined by the rate of rotation of the fluid-analysis disk or by acceleration in the rate of rotation of the fluid-analysis disk, wherein the fluid-analysis disk is configured to release the fluid from the first reservoir when the fluid-analysis disk reaches a first rotation or rotation-acceleration rate, wherein the fluid-analysis disk is configured to release the fluid from the second reservoir when the fluid-analysis disk reaches a second rotation or rotation-acceleration rate distinct from the first rotation or rotation-acceleration rate, and wherein the fluid-analysis disk is characterized by at least one of the following:

a) the outlet of the first reservoir faces a first direction relative to the central axis, and the outlet of the second reservoir faces a second direction relative to the central axis, wherein the second direction differs from the first direction;

b) the first reservoir is offset from the central axis of the fluid-analysis disk by a first radius, wherein the second reservoir is offset from the central axis of the fluid-analysis disk by a second radius that is less than the first radius; and c) the first stopper in the first reservoir has a first release or sealing force, and the second stopper in the second reservoir has a second release or sealing force, wherein the first release or sealing force is less than the second release or sealing force.

2. The apparatus of claim 1, further comprising a particle collector mountable opposite the peripheral outlet of the aerosol-collection disk.

3. The apparatus of claim 2, wherein the particle collector includes at least a segment of an annular band to which particles can adhere upon contact.

4. The apparatus of claim 1, wherein the outlet of the first reservoir faces the first direction relative to the central axis, and the outlet of the second reservoir faces the second direction relative to the central axis, wherein the second direction differs by at least 5° from the first direction.

5. The apparatus of claim 1, wherein the first reservoir is offset from the central axis of the disk by the first radius, and the second reservoir is offset from the central axis of the disk by the second radius, which is at least 5% less than the first radius.

6. The apparatus of claim 1, wherein the release or sealing force of the first stopper in the first reservoir is at least 5% less than the release or sealing force of the second stopper in the second reservoir.

7. The apparatus of claim 6, wherein the release or sealing force includes at least one of the following forces: stiction, plunging spring force, mechanical detent, and plunger inertia.

8. The apparatus of claim 1, wherein at least one stopper comprises a plunger that seals the outlet or the reservoir and a mechanism mounted to the plunger and to the disk to maintain the plunger in the outlet.

9. The apparatus of claim 8, wherein the mechanism is a spring.

10. The apparatus of claim 1, wherein at least one stopper comprises a viscous plug filling the outlet.

11. The apparatus of claim 1, wherein the aerosol-collection disk is distinct from the fluid-analysis disk.

12. The apparatus of claim 1, wherein the aerosol-collection disk defines an inlet at its center and channels extending radially from the central inlet to an outer diameter of the aerosol-collection disk and is configured to generate a flow of aerosol from the central inlet through the channels to the outer diameter when rotated.

13. The apparatus of claim 1, wherein the fluid-analysis disk is configured to release at least one of the fluids as the rotation or rotation-acceleration rate increases.

14. The apparatus of claim 1, wherein the fluid-analysis disk is configured to release at least one of the fluids as the rotation or rotation-acceleration rate decreases.

* * * * *